United States Patent [19]

Takahashi et al.

[11] 4,345,016

[45] Aug. 17, 1982

[54] COLOR PHOTOGRAPHIC SENSITIVE MATERIAL

[75] Inventors: Osamu Takahashi; Nobutaka Ohki; Kozo Aoki, all of Minami-ashigara, Japan

[73] Assignee: Fuji Photo Film Co., Ltd., Kanagawa, Japan

[21] Appl. No.: 279,382

[22] Filed: Jul. 1, 1981

[30] Foreign Application Priority Data

Jul. 4, 1980 [JP] Japan ................................. 55/91571

[51] Int. Cl.³ .............................................. G03C 5/54
[52] U.S. Cl. ..................... 430/214; 430/215; 430/217; 430/223; 430/545; 430/551; 430/559; 430/629; 430/634
[58] Field of Search ............... 430/214, 213, 215, 217, 430/223, 372, 377, 545, 551, 559, 634, 636, 629

[56] References Cited

U.S. PATENT DOCUMENTS

| | | | |
|---|---|---|---|
| 2,710,801 | 6/1955 | Minsk et al. | 430/372 |
| 2,816,028 | 12/1957 | Minsk | 430/551 |
| 3,698,897 | 10/1972 | Gompf et al. | 430/223 |
| 3,772,014 | 11/1973 | Scullard | 430/214 |
| 4,277,553 | 7/1981 | Onodera et al. | 430/551 |

Primary Examiner—J. Travis Brown

Attorney, Agent, or Firm—Sughrue, Mion, Zinn, Macpeak & Seas

[57] ABSTRACT

A color photographic sensitive material containing a polymer comprising at least 1 mol % of a repeating unit represented by formula (I)

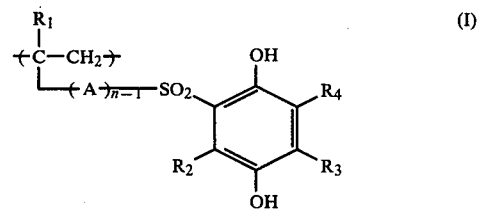

wherein A represents a divalent group, n is 1 or 2, $R_1$ represents hydrogen, a halogen atom or an alkyl group, and $R_2$, $R_3$, and $R_4$ each represents hydrogen, a halogen atom, an alkyl group, an aryl group, an alkoxy group, an aryloxy group, an alkylthio group, an arylthio group, an amino group, an acylamino group, or a sulfonamide group, and $R_3$ and $R_4$ together can form an aromatic ring, provided that the total of carbon atoms of $R_2$, $R_3$, and $R_4$ is 60 or less.

22 Claims, No Drawings

COLOR PHOTOGRAPHIC SENSITIVE MATERIAL

FIELD OF THE INVENTION

The present invention relates to color photographic sensitive materials, and particularly to color photographic sensitive materials containing a polymer comprising sulfonyl hydroquinone moieties as a scavenger for oxidized developing agent.

BACKGROUND OF THE INVENTION

It has been known that a "color fogging" phenomenon is caused in color photographic sensitive materials comprising a silver halide photographic sensitive material containing a compound capable of releasing a diffusible dye by a redox reaction caused by development (usually referred to as a "dye releasing redox" compound) which are developed using a black-and-white developing agent such as phenidone, etc., and in color photographic sensitive materials containing couplers which are developed using a color developing agent, and it has been well known that various kinds of oxidized developing agent scavengers are used for preventing this phenomenon.

In the case of multicolor photography, the above-described oxidized developing agent scavenger is used in an intermediate layer in order to obtain good color separation, or is used in a silver halide emulsion layer or a dye image donator layer (for example, a layer containing a dye releasing redox compound or a coupler) combined with the silver halide emulsion layer in order to obtain a minimum density of fogging.

As the above-described oxidized developing agent scavenger, it has been known hitherto to use various substituted hydroquinones. For example, the use of monosubstituted alkyl hydroquinones has been described in U.S. Pat. Nos. 2,360,290, 2,418,613, 2,403,721 and 3,960,570, etc., and the use of monobranched alkyl hydroquinones in U.S. Pat. No. 3,700,453, German Patent Application (OLS) No. 2,149,789 and Japanese Patent Applications (OPI) Nos. 156438/75 and 106329/74 (the term "OPI" as used herein refers to a "published unexamined Japanese patent application"). On the other hand, the use of disubstituted alkylhydroquinones has been described in U.S. Pat. Nos. 2,728,659, 2,732,300 and 3,243,294, British Pat. No. 752,146 and *Chemical Abstracts*, Vol. 56, 6367h, and the use of dibranched alkylhydroquinones in U.S. Pat. Nos. 3,700,453, 2,732,300 and 3,243,294, the above-described Chemical Abstracts, Japanese Patent Applications (OPI) Nos. 156438/75, 9528/78 and 29637/79 and Japanese Patent Publication No. 21249/75.

In addition, the use of substituted hydroquinones as an oxidized developing agent scavenger has been described in U.S. Pat. Nos. 2,701,197, 2,710,801, and 2,704,713 and *Research Disclosure*, 12245 (1974), etc.

Further, the use of polymers having hydroquinone moieties as an oxidized developing agent scavenger has been described in U.S. Pat. Nos. 2,710,801, and 2,816,028.

It is desirable that the oxidized developing agent scavenger used for a multicolor photographic process, and particularly for a color diffusion transfer process, should satisfy the following requirements.

(1) It should be a compound capable of suitably reacting with an oxidized developing agent formed by development of silver halide. For example, a compound to be incorporated in an intermediate layer is added to the intermediate layer placed between a silver halide layer and a layer containing a dye releasing redox compound (or a coupler) which is not associated with the emulsion layer in order to prevent reacting the oxidized developing agent formed by development of silver halide with the dye releasing redox compound (or the coupler) which is not combined with said silver halide. In this case, it is necessary that the compound reacts with the oxidized developing agent to capture it, by which diffusion thereof into the "layer containing a dye releasing redox compound (or a coupler) which is not combined" is substantially prevented.

Furthermore, in the case wherein the reactivity of the compound with the oxidized developing agent is too high, it is desirable that the reaction should be suitably carried out in order to reduce the maximum dye image density by preventing the reaction of the oxidized developing agent formed by development of silver halide with the dye releasing redox compound (or a coupler) "which is combined" with said silver halide.

(2) An increase of the thickness of the sensitive material should be small in case of adding the oxidized developing agent scavenger to the sensitive material. In case of a color diffusion transfer process, it is sometimes necessary that a dye released from the dye releasing redox compound passes through a layer containing the oxidized developing agent scavenger. The thickness of the layer containing the oxidized developing agent scavenger can be decreased when the amount of the oxidized developing agent scavenger and the amount of materials required for adding the oxidized developing agent scavenger (a high boiling point solvent and gelatin, etc.) are decreased. Consequently, the time necessary to pass the released dye through the layer becomes short and sharpness of transfer images is improved. In an instant color diffusion transfer process for forming images as quickly as possible, it is very important to decrease the thickness to the minimum value possible.

(3) Influence upon the silver developing property of the silver halide emulsion should be small when the oxidized developing agent scavenger is added to the photosensitive material. Particularly, in the case of carrying out development wherein a direct positive image is formed using an inner latent image type silver halide emulsion, the oxidized developing agent scavenger existing in the silver halide emulsion layer or a layer adjacent to the silver halide emulsion layer sometimes has an adverse influence upon the silver developing property. Accordingly, it is necessary to use a compound which has a smaller influence upon it.

(4) It should not reduce a diffusible dye or a diffusible dye precursor to change the color hue in the case of carrying out a development processing at a high pH. Particularly, some dialkylhydroquinones (for example, 2,5-di-sec-dodecylhydroquinone and 2,5-di-tert-pentadecylhydroquinone) used as an oxidized developing agent scavenger sometimes cause a change of hue of compounds having a dye constitution moiety containing a reducible group (for example, a nitro group) in a dye structural part. Since such a change of the hue has a significant adverse influence upon color reproduction, it is very important to appropriately select the oxidized developing agent scavenger to be combined with a compound having a dye constitution moiety containing a reducible group in the dye structural part (for example, monoazonaphthol dyes having a nitro group).

(5) It should not produce a photographically undesirable effect by migrating into each layer of the color photographic sensitive material. It is necessary that an undesirable effect is not substantially produced before, during, and after the processing of the color photographic sensitive material.

(6) It should not cause deterioration of interlayer adhesion. Generally, when a high boiling point solvent or a hydroquinone derivative which is liquid at room temperature is added to the sensitive material, the interlayer adhesion deteriorates. Accordingly, it is desirable that such a phenomenon does not occur.

(7) It should have a minimal dependence on the processing temperature of the development (i.e., it should have a wide latitude of temperature for the development processing). Particularly, it is necessary for a color diffusion transfer process that the photographic sensitivity is high, the maximum density is sufficiently high, the minimum density is sufficiently low, and the gradation is suitable, even if the processing temperature varies.

(8) The quality of coated materials should not be deteriorated by separation of crystals during or after application, and colored by-products should not be formed during application or processing by an oxidation reaction.

The present invention is based on discoveries of a polymer compound satisfying the above-described requirements for the oxidized developing agent scavenger, and a process for using the polymer compound.

SUMMARY OF THE INVENTION

Accordingly, the first object of the present invention is to provide a novel oxidized developing agent scavenger suitable for producing thin layer type sensitive materials without creating adverse effects (e.g., interlayer migration, inferior adhesion, and separation of crystals) which provides a high transfer dye density without having an adverse influence upon the silver developing property of the silver halide, by which the time for forming complete images can be shortened and color fogging can be effectively prevented.

A second object of the present invention is to provide an oxidized developing agent scavenger which does not cause undesirable effects (for example, a change of hue) even if processed with a processing solution having a high pH, such as in a color diffusion transfer process.

A third object of the present invention is to provide color photographic sensitive materials containing the above-described oxidized developing agent scavenger.

A fourth object of the present invention is to provide color photographic sensitive materials containing the above-described oxidized developing agent scavenger which have an inner latent image type silver halide emulsion layer combined with a dye image forming material for providing a transfer image by a diffusible dye (for example, a dye releasing redox compound).

These and other objects of the present invention will be understood by the following detailed explanation of the invention.

The above objects of the present invention have been attained by incorporating a homopolymer or a copolymer comprising a repeating unit represented by formula (I) in a color photographic sensitive material.

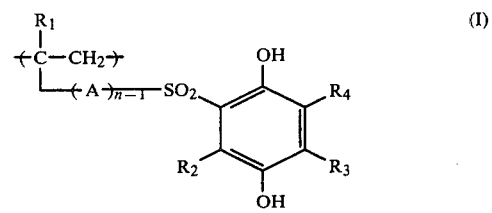

In the formula, A represents a divalent group [preferably having from 1 to 12 carbon atoms, for example, a phenylene group such as a p-phenylene group or an m-phenylene group, etc., an alkylene group such as an ethylene group or an n-propylene group, etc.,

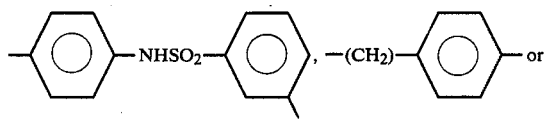

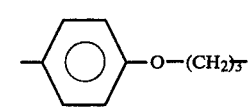

(for ease of synthesis, the bonds at the right-hand side of the foregoing groups are connected to the —SO₂— moiety of the repeating unit of formula (I)], and n is 1 or 2. $R_1$ represents hydrogen, a halogen atom, or an alkyl group (preferably having from 1 to 6 carbon atoms, for example, a methyl group or an ethyl group, etc.), and $R_2$, $R_3$ and $R_4$ represent each hydrogen, a halogen atom or an alkyl group (preferably having from 1 to 32 carbon atoms, for example, a methyl group, a tert-butyl group, a sec-octyl group, a tert-octyl group, an n-pentadecyl group or a sec-eicosyl group, etc.), an alkenyl group (preferably having 1 to 20 carbon atoms, for example, an allyl group, etc.), an aryl group (preferably having from 6 to 20 carbon atoms, for example, a phenyl group, a p-tolyl group, or a naphthyl group, etc.), an alkoxy group (preferably having 1 to 20 carbon atoms, for example, a methoxy group, an n-butoxy group, or a tert-butoxy group, etc.), an aryloxy group (preferably having from 6 to 20 carbon atoms, for example, a phenoxy group, etc.), an alkylthio group (preferably having from 1 to 32 carbon atoms, for example, an n-octylthio group or an n-dodecylthio group, etc.), an arylthio group (preferably having from 6 to 20 carbon atoms, for example, a phenylthio group, etc.), an amino group (preferably having from 0 to 20 carbon atoms, for example, an amino group, a hexylamino group or a dimethylamino group, etc.), an acylamino group (preferably having from 2 to 20 carbon atoms, for example, an acetylamino group or a lauroylamino group, etc.) or a sulfonamide group (preferably having from 1 to 20 carbon atoms, for example, a methylsulfonamide group, etc.) which may be substituted or unsubstituted, respectively. Each of the alkyl group, alkenyl group, aryl group, alkoxy group, aryloxy group, alkylthio group and arylthio group in the above-described $R_2$, $R_3$ and $R_4$ may be substituted by suitable substituents. Examples of preferred substituents include halogen atoms, alkyl groups, aryl groups, alkoxy groups, a carboxyl group, a sulfo group and a hydroxy group, etc. The carbon ranges described above include the carbon atoms of substituents, if substitution occurs, and are total carbon numbers. Preferred substituents in the amino group, acylamino group and sulfonamide group in the above-described $R_2$, $R_3$ and $R_4$ are alkyl groups. Further, $R_3$ and $R_4$ together can form an aromatic ring, and, preferably, they form together a 5- to 7-membered carbocyclic ring (for example, a cyclopentane ring, a cyclohexane ring, a cyclohexadiene ring, or a norbornene ring, etc.). The total number of carbon atoms of $R_2$, $R_3$, and $R_4$ is 60 or less, and preferably 3 to 32.

The homopolymer or copolymer comprising the repeating unit (I) is preferably immobilized (i.e., not transferable) into a layer adjacent to a layer in which the homo- or copolymer is incorporated.

In general, polymers of hydroquinone type are dispersed in a solvent only with difficulty. However, the homo- or copolymers used in this invention are easily dispersed in a solvent.

DETAILED DESCRIPTION OF THE INVENTION

In the present invention, it is preferred that A in formula (I) is a phenylene group. It is further preferred that A is a phenylene group and $R_1$ is hydrogen. Still further, it is preferred that A is a phenylene group, $R_1$ is hydrogen, and n is 2. In another preferred embodiment, A is a phenylene group, $R_1$ and $R_2$ are each hydrogen, and one of $R_3$ and $R_4$ is a substituent other than hydrogen and the other is hydrogen atom. In a further preferred embodiment, $R_1$ and $R_2$ are each hydrogen, A is a p-phenylene group, n is 2, and one of $R_3$ and $R_4$ is a substituent other than hydrogen and the other is hydrogen. Furthermore, in these preferred embodiments, it is preferred that the above-described substituent other than hydrogen is a substituted or unsubstituted alkyl group (preferably having 20 carbon atoms or less). The carbon atom number is preferred to be in the range of from 3 to 20 if $R_3$ is the alkyl group.

Furthermore, it is preferred that the polymer comprising a repeating unit represented by formula (I) also comprises a repeating unit represented by formula (IA)

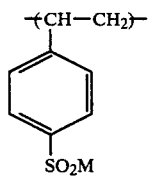  (IA)

In the formula, M represents hydrogen or a cation.

Preferably, the repeating unit represented by formula (IA) constitutes from about 1 to about 50 mol% of the polymer.

As processes for synthesizing homopolymer or copolymer comprising a repeating unit represented by formula (I), the following two processes (a) and (b) are preferably utilized (because hydroquinones are polymerization inhibitors).

Process (a):

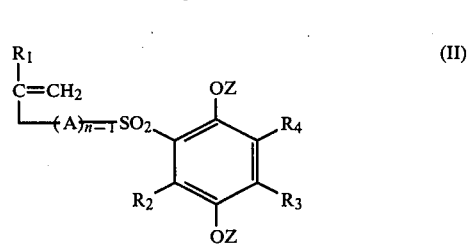  (II)

First, a compound represented by the above formula (II) is synthesized. Synthesis of a compound represented by formula (II) and synthesis of a polymer therefrom by the process (a) can be carried out as described in *Die Macromolekulare Chemie,* Vol. 123 (1969), page 223, and Vol. 134 (1970), page 231, and *Canadian Journal of Chemistry,* Vol. 41 (1963), page 483. Then, after carrying out homopolymerization or copolymerization, the protective group Z is removed.

In formula (II), A, n, $R_1$, $R_2$, $R_3$ and $R_4$ each has the same meaning as those symbols used in formula (I). Z represents a group known as a protective group for phenolic-OH, for example, an acetyl group, a tetrahydropyran-2-yl group, and other protective groups as described in *Protective Groups in Organic Chemistry,* edited by V. F. W. McOmie, Plenum Press (1973), hereby incorporated by reference.

Process (b):

  (III)

  (IV)

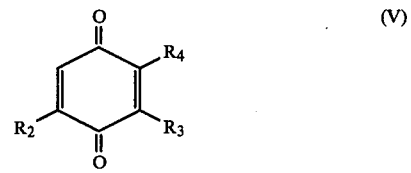  (V)

First, a compound represented by formula (III) is synthesized (A process for synthesizing compounds represented by formula (III) is described, for example, in *Chemistry Letters,* page 419 (1976). Synthesis of similar monomers can be carried out by the analogous process as that described in the above-described *Chemistry Letters* (e.g., such a synthesis is applicable to preparation of

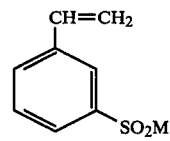

or by a process which comprises reducing with a reducing agent such as sodium sulfite and, if necessary, carrying out vinylation, after the corresponding sulfonyl chloride was synthesized), which is then subjected to homopolymerization or copolymerization to derive the polymer having a repeating unit represented by formula (IV). Thereafter, the sulfinic acid moiety is added to the quinone represented by formula (V), to produce a polymer having a repeating unit represented by the formula (I). The 1,4-benzoquinones represented by formula (V) can be produced by a process which comprises oxidizing 1,4-hydroquinones with manganese dioxide (*J. Indian Chem. Soc.*, Vol. 14, 291 (1937)), a process which comprises oxidizing phenols with persulfate (*Indian J. Chem.*, 1971, 950) or a process which comprises oxidizing aminophenols with nitrous acid (*Org. Synth. Coll.*, Vol. 1, p. 511 (1956)), etc. The addition reaction of the polymer represented by formula (IV) with the 1,4-benzoquinone represented by formula (V) can be carried out according to processes as described in *Canadian Journal of Chemistry*, Vol. 42, page 554 (1964), U.S. Pat. No. 3,698,897, *Tetrahedron*, Vol. 25, page 2715 (1969) and *Tetrahedron*, Vol. 26, page 731 (1970), etc.

In formulae (III), (IV) and (V), M represents hydrogen or a cation (for example, sodium, potassium, calcium, barium, ammonium or triethylammonium, etc.) and A, n, $R_1$, $R_2$, $R_3$ and $R_4$ each has the same meaning as those symbols used in formula (I).

In the above-described two processes (a) and (b) for producing polymers represented by formula (I), the process (a) is advantageous for emulsion polymerization, because the monomers represented by formula (III) have a comparatively high hydrophobic property. Further, in the case of carrying out the process (b), highly hydrophilic polymers can be easily obtained by leaving a part of sulfinic acid moieties of the polymers represented by formula (IV) in an unreacted state. In this latter case, it is possible to immobilize the polymers by cross-linking, such as by reacting the sulfinic acid moieties with a compound known as a gelatin hardener (for example, a bifunctional active vinyl compound, a bifunctional active halogen compound or aldehyde, etc.).

As comonomers capable of introduction into the chain of the repeating unit (I) by the process (a) or the process (b), namely, as monomers capable of copolymerizing with the monomers (II) or (III), any monomers can be generally used if they have at least one addition-polymerizable unsaturated bond (i.e., addition-polymerizable unsaturated compounds). Examples of such addition-polymerizable unsaturated compounds include allyl compounds such as allyl esters (for example, allyl acetate, allyl caproate, allyl caprylate, allyl laurate, allyl palmitate, allyl stearate, allyl benzoate, allyl acetoacetate and allyl lactate, etc.) and allyl ethers (for example, allyl butyl ether, allyl glycidyl ether and allyl phenyl ether), etc.; vinyl ethers (for example, methyl vinyl ether, hexyl vinyl ether, octyl vinyl ether, decyl vinyl ether, ethylhexyl vinyl ether, methoxyethyl vinyl ether, ethoxyethyl vinyl ether, chloroethyl vinyl ether, 1-methyl-2,2-dimethylpropyl vinyl ether, 2-ethyl butyl ether, hydroxyethyl vinyl ether, diethylene glycol vinyl ether, dimethylaminoethyl vinyl ether, diethylaminoethyl vinyl ether, butylaminoethyl vinyl ether, benzyl vinyl ether, tetrahydrofurfuryl vinyl ether, vinyl phenyl ether, vinyl tolyl ether, vinyl chlorophenyl ether, vinyl naphthyl ether and vinyl anthranyl ether, etc.); vinyl esters such as vinyl acetate, vinyl propionate, vinyl butyrate, vinyl isobutyrate, vinyl dimethylpropionate, vinyl ethylbutyrate, vinyl valerate, vinyl caproate, vinyl chloroacetate, vinyl dichloroacetate, vinyl methoxyacetate, vinyl butoxyacetate, vinyl phenylacetate, vinyl acetoacetate, vinyl lactate, vinyl β-phenylbutyrate, vinyl cyclohexylcarboxylate, vinyl benzoate, vinyl salicylate, vinyl chlorobenzoate, vinyl tetrachlorobenzoate or vinyl naphthoate, etc.; vinyl heterocyclic compounds such as N-vinyloxazolidone, N-vinylimidazole, N-vinylpyrrolidone, N-vinylcarbazole, vinylthiophene or N-vinylethylacetoamide, etc.; styrenes (for example, styrene, divinylbenzene, methylstyrene, dimethylstyrene, trimethylstyrene, ethylstyrene, diethylstyrene, isopropylstyrene, butylstyrene, hexylstyrene, cyclohexylstyrene, decylstyrene, benzylstyrene, chloromethylstyrene, trifluoromethylstyrene, ethoxymethylstyrene, acetoxymethylstyrene, methoxystyrene, 4-methoxy-3-methylstyrene, dimethoxystyrene, chlorostyrene, dichlorostyrene, trichlorostyrene, tetrachlorostyrene, pentachlorostyrene, bromostyrene, dibromostyrene, iodostyrene, fluorostyrene, trifluorostyrene, 2-bromo-4-trifluoromethylstyrene, 4-fluoro-3-trifluoromethylstyrene and vinyl benzoic acid methyl ester, etc.); crotonic acid compounds such as crotonic acid, crotonamide, or crotonic acid esters (for example, butyl crotonate, hexyl crotonate and glycerine monocrotonate, etc.); vinyl ketones (for example, methyl vinyl ketone, phenyl vinyl ketone and methoxyethyl vinyl ketone, etc.); olefins (for example, dicyclopentadiene, ethylene, propylene, 1-butane, 1-pentene, 1-hexene, 4-methyl-1-pentene, 1-heptene, 1-octene, 1-decene, 5-methyl-nonene, 5,5-dimethyl-1-octene, 4-methyl-1-hexene, 4,4-dimethyl-1-pentene, 5-methyl-1-hexene, 4-methyl-1-heptene, 5-methyl-1-heptene, 4,4-dimethyl-1-hexene, 5,6,6-trimethyl-1-heptene, 1-dodecene and 1-octadecene, etc.); itaconic acid compounds (for example, itaconic acid, itaconic acid anhydride, methyl itaconate and ethyl itaconate), sorbic acid, cinnamic acid, methyl sorbate, glycidyl sorbate, citraconic acid, chloroacrylate, mesaconic acid, maleic acid, fumaric acid, ethacrylic acid, halogenated olefins (for example, vinyl chloride, vinylidene chloride and isoprene, etc.), unsaturated nitriles (for example, acrylonitrile and methacrylonitrile, etc.), acrylic acids such as acrylic acid or methyl acrylate, methacrylic acids such as methacrylic acid or methyl methacrylate, acrylamides, methacrylamides, etc.

Among these addition-polymerizable unsaturated compounds, it is particularly preferred to use styrenes, vinyl heterocyclic compounds, vinyl ethers, vinyl esters and olefins.

The polymers capable of using in the present invention necessary to contain the repeating unit represented by formula (I) in an amount of at least 1 mol%, preferably at least 5 mol%, and more preferably at least 20 mol%. Furthermore, these polymers are preferred to have an average molecular weight of from 1,000 to 4,000,000, and more preferably from 10,000 to 1,000,000. If the molecular weight is too low, diffusion resistance is inferior. If it is too high, the viscosity of the coating solution sometimes becomes too high when the polymer is added.

Examples of the polymers used in the present invention are described below, but the present invention is not limited to them. Ratios of the composition are shown on a molar ratio basis.

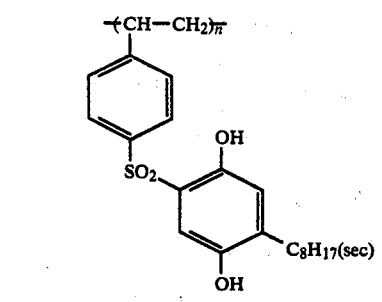 (1)
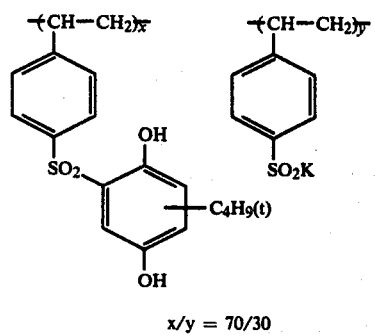 (2)
x/y = 70/30
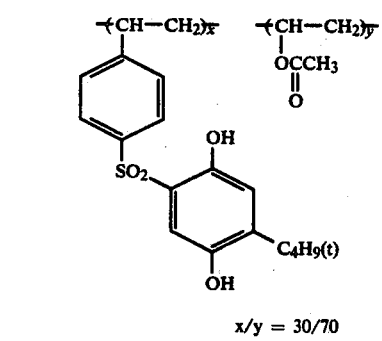 (3)
x/y = 30/70
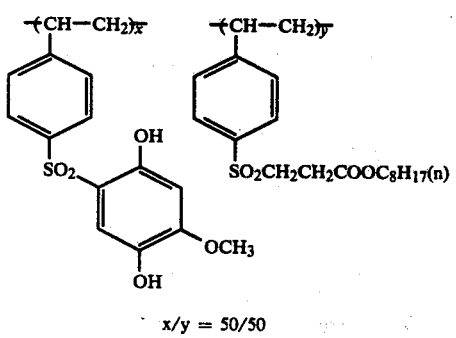 (4)
x/y = 50/50
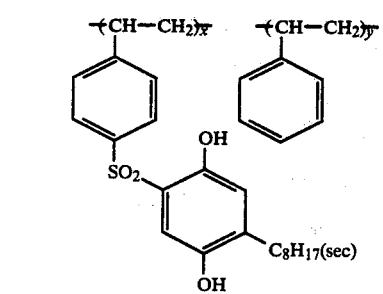 (5)
x/y = 80/20
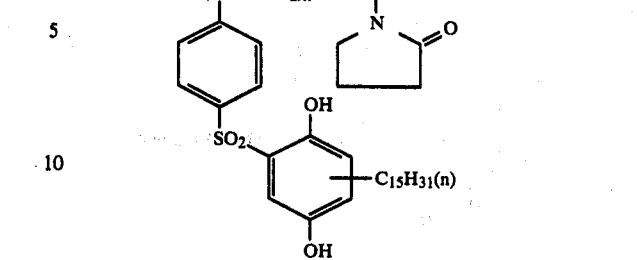 (6)
x/y = 60/40
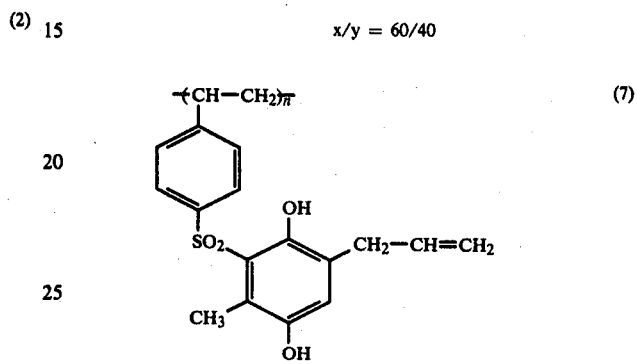 (7)
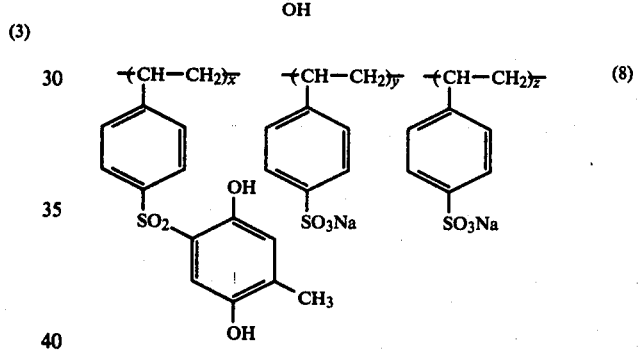 (8)
x/y/z = 50/20/30
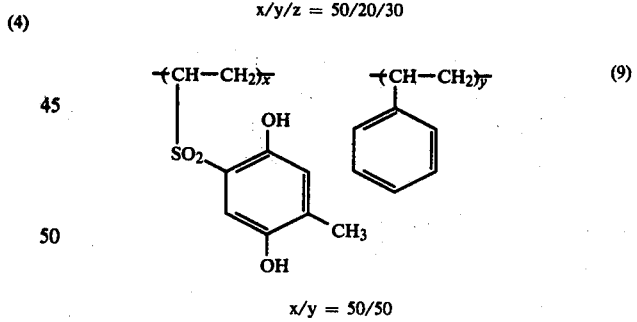 (9)
x/y = 50/50
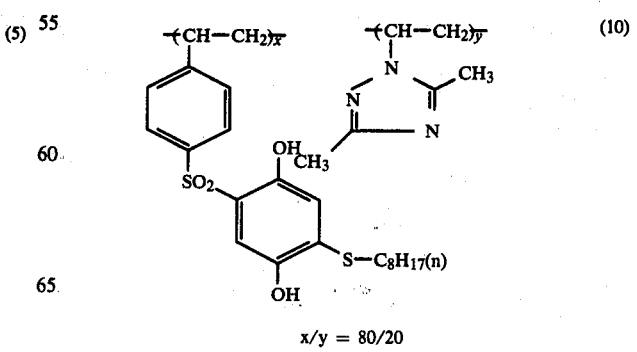 (10)
x/y = 80/20

-continued
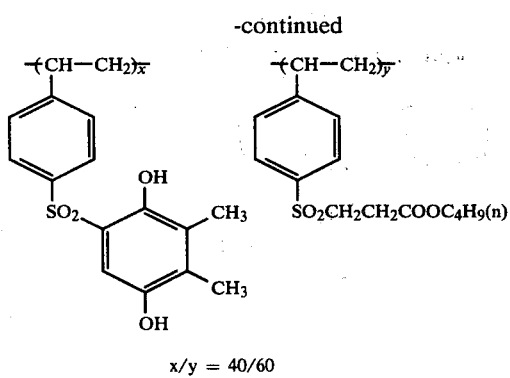
(11)
x/y = 40/60
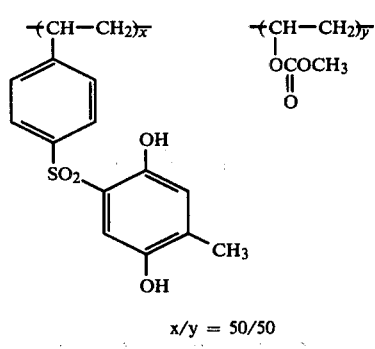
(12)
x/y = 50/50
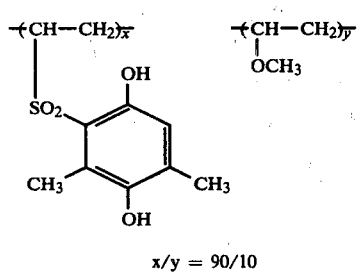
(13)
x/y = 90/10
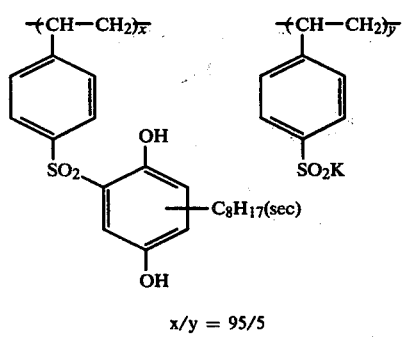
(14)
x/y = 95/5
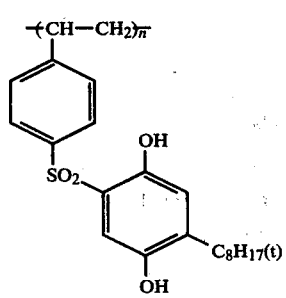
(15)
-continued
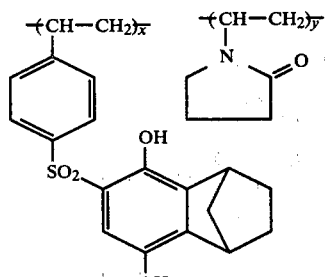
(16)
x/y = 70/30
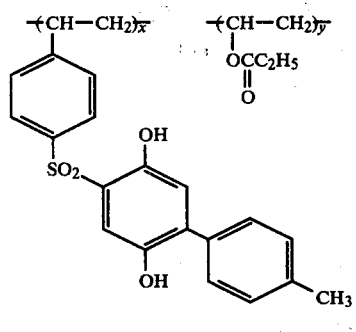
(17)
x/y = 80/20
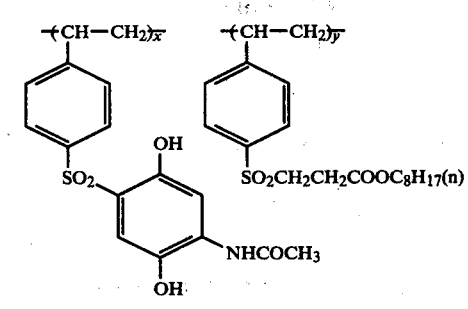
(18)
x/y = 60/40
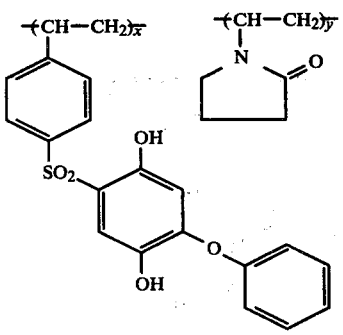
(19)
x/y = 50/50

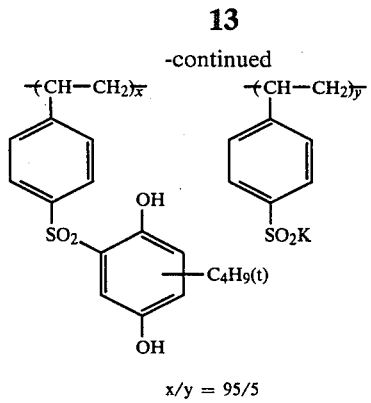

$$x/y = 95/5 \quad (20)$$

Below, an example of synthesis of a polymer compound useful in the present invention is described, but the invention is not limited thereto.

Example of Synthesis (by Process (b))

Synthesis of poly-[4-(2,5-dihydroxy-x-tert-butylphenyl)sulfonylstyrene-co-potassium-4-vinylbenzenesulfinate]

(Compound (20))

(1) Synthesis of p-(β-bromoethylbenzene)sulfonyl chloride

A 3-neck flask equipped with a stirrer was charged with 84.3 g of 30% fuming sulfuric acid and a mixture composed of 58.8 g (0.32 mol) of β-bromoethylbenzene and 26.1 g (0.636 mol) of acetonitrile was added dropwise thereto while maintaining the liquid solution at from 20° C. to 23° C. After conclusion of the addition, the temperature of the reaction solution was raised to from 40° C. to 45° C. and 92.3 g (0.795 mol) of chlorosulfonic acid was added dropwise at this temperature. After conclusion of the addition, the temperature of the reaction solution was maintained for about 30 minutes at from 40° C. to 45° C. to conclude the reaction. The reaction solution was then poured into 1 liter of ice-water and precipitated crystals were separated by filtration. After drying, they were recrystallized from hexane. The yield was 59% and the melting point was 54°-55° C.

(2) Synthesis of p-(β-bromoethylbenzene)sulfinic acid 42.5 g (0.15 mol) of p-(β-bromoethylbenzene)sulfonyl chloride obtained from the above-described reaction (1) was placed in a 500 cc 3-neck flask together with 210 cc of glacial acetic acid, 12.8 g of zinc powder was added thereto at 25°-35° C. with stirring. After conclusion of the addition, the mixture was stirred at 35° C. for 1 hour. Thereafter, 128 ml of concentrated hydrochloric acid and 106 ml of water were added thereto and the liquid temperature was raised to about 80° C. After conclusion of the reaction, the reaction solution was cooled with ice and the resulting crystals were separated by filtration and recrystallized with water. The yield was 42% and the melting point was 105°-107° C.

(3) Synthesis of potassium 4-vinylbenzenesulfinate 12.7 g (0.051 mol) of 2-bromoethylbenzenesulfinic acid obtained by the above-described reaction (2), 10.0 g (0.153 M) of caustic potash, 237 ml of methanol and 0.14 g of hydroquinone were put in a 500 cc 3-neck flask. After carrying out refluxing for 1 hour, methanol was evaporated to dryness, to which 80 ml of water and 9 ml of concentrated hydrochloric acid were added. The resulting solution was cooled with ice and crystals of vinylbenzenesulfinic acid were separated by filtration. The crystals were dissolved in water and neutralized with caustic potash. Then water was removed by distillation to obtain the desired product. Yield: 60%. Melting point: more than 200° C.

(4) Synthesis of poly-(potassium vinylbenzenesulfinate)

A 100 cc 3-neck flask was charged with 54 g of distilled water and the water was degassed by a nitrogen gas and heated to 80° C. under a nitrogen stream. Then, 6.0 g (0.029 mol) of potassium vinylbenzenesulfinic acid obtained by the above-described reaction was added thereto. After dissolution, 0.15 g of 2,2'-abozis(2-amidinopropane) hydrochloride was added thereto. After continued stirring at 80° C. for 4 hours, the solution was cooled to room temperature to obtain an aqueous solution of 10% by weight poly(potassium vinylbenzenesulfinate).

(5) Synthesis of 2-tert-butyl-1,4-benzoquinone 16.6 g (0.10 mol) of 2-tert-butylhydroquinone was placed in a 200 cc 3-neck flask. After adding 17.4 g (0.20 mol) of powdery manganese dioxide, 100 cc of toluene was added thereto, and the mixture was heated with stirring. The temperature was maintained at 70° C. for 3 hours. After cooling to room temperature, the manganese dioxide was removed by filtration by means of suction using Celite as a filter aid. Then the manganese dioxide was washed with 50 cc of toluene, and the toluene was evaporated to dryness, by which 2-tert-butyl-1,4-benzoquinone was obtained. The yield was 80% and the melting point was 48°-50° C.

(6) Synthesis of poly-[4-(2,5-dihydroxy-x-tert-butyl)-sulfonyl-styrene-co-potassium 4-vinylbenzenesulfinate] (Compound (20)):

60 g of an aqueous solution of 10% by weight of poly(potassium 4-vinylbenzenesulfinate) obtained by the above-described reaction (4) was placed in a 500 cc three-necked flask equipped with a condenser. After adding 120 cc of methanol and 6 cc of acetic acid, the mixture was heated with stirring and kept at 50° C. 4.5 g of tert-butyl-1,4-benzoquinone obtained by the above-described reaction (5) was dissolved in 60 cc of methanol and added dropwise to the mixture. After 30 cc of the quinone solution was added dropwise over 20 minutes, 60 cc of ethyl acetate was added to the flask. When the temperature of the content returned to 50° C., 15 cc of the quinone solution was added dropwise over 10 minutes. 60 cc of ethyl acetate was added again to the flask. After the temperature of the content became 50° C., the balance of the quinone solution was added over 10 minutes. After the stirring was continued for about 15 minutes, then the mixture was cooled to room temperature. The solution was evaporated to dryness, and the resulting solid was dissolved in 200 cc of methanol. The solution was poured slowly into 1,000 cc of water with stirring, and the resulting flaky solid was separated by filtration, followed by drying, to obtain 8.1 g of the desired product (Compound (20)) as a milk-white powder.

The oxidized developing agent scavengers according to the present invention may be used as a mixture of two kinds of them in a suitable ratio. Further, they may be used together with other hydroquinone derivatives, as described hereinbefore.

The oxidized developing agent scavengers according to the present invention may be incorporated in various layers in a sensitive material, for example, a silver halide emulsion layer (a blue-sensitive emulsion layer, a green-sensitive emulsion layer, or a red-sensitive emulsion layer) or an adjacent layer thereof (for example, an intermediate layer or a layer containing a dye image forming material), a carbon black layer, a light reflection layer, etc. Preferably, they are incorporated in the silver halide emulsion layer, the intermediate layer, or the layer containing a dye image forming material and, particularly, in the intermediate layer.

The amount of the oxidized developing agent scavengers according to the present invention depends upon the purpose of using the sensitive material, the kind of the dye image forming compound (for example, the dye releasing redox compound or the coupler), the kind of the silver halide emulsion, the layer construction and the development processing, etc. In the case of adding to the layer containing a dye image forming compound or the silver halide layer, it is preferred to add in such an amount that the equivalent of hydroquinone moiety is from 0.1 to 100 mol%, and preferably from 1 to 30 mol%, based on the dye image forming compound. In the case of adding to a layer different from the layer containing a dye image forming material, it is preferred to add in such an amount that the equivalent of the hydroquinone moiety is from 1 to 1,000 mol%, and preferably from 10 to 600 mol%, based on the dye image forming compound.

The silver halide emulsions used in the present invention are hydrophilic colloid dispersion of silver chloride, silver bromide, silver chlorobromide, silver iodobromide, silver chloroiodobromide or mixtures thereof. Although the halogen composition of them is selected according to the particular purpose of using the sensitive material and processing conditions thereof, it is generally preferable to use silver bromide, silver iodobromide and silver chloroiodobromide wherein the iodide content is 10 mol% or less and the chloride content is 30 mol% or less.

Inner latent image type silver halide emulsions advantageously used in the present invention are described, e.g., in U.S. Pat. Nos. 2,592,250, 3,206,313, 3,447,297, 3,761,276 and 3,935,014, etc.

Typical fogging agents for this type of emulsion include hydrazines as described in U.S. Pat. Nos. 2,588,982 and 2,563,785, hydrazides and hydrazones as described in U.S. Pat. No. 3,227,552, and quaternary salt compounds as described in British Pat. No. 1,283,835, Japanese Patent Publication No. 38164/74 and U.S. Pat. Nos. 3,734,738, 3,719,494 and 3,615,615.

The silver halide emulsions used in the present invention may have a color sensitivity provided, if desired, by spectral sensitizing dyes.

Various compounds can be utilized as the dye image donative compounds used in the present invention, but dye releasing redox compounds and couplers are particularly useful.

Examples of useful dye releasing redox compounds include those described in, for example, Japanese Patent Applications (OPI) Nos. 33826/73, 126331/74, 104343/76, 46730/76, 113624/76 and 47823/78, Research Disclosure, Vol. 151, No. 15157 (November 1976), Vol. 130, No. 13024 (February 1975) and Vol. 156, No. 15654 (April 1977) and Japanese Patent Applications (OPI) Nos. 111628/74 and 63618/76.

In carrying out the present invention, it is preferred to use dye releasing redox compounds represented by the formula $$Y—X$$

In the formula, Y represents a redox nucleus (carrier) and X represents a dye moiety or a dye precursor moiety bonding to Y directly or through a linking group L.

L represents a linking group such as an alkylene group (or an alkylidene group) having from 1 to 6 carbon atoms, an arylene group or a heterocyclic group, which bonds to X directly or through —O—, —S—, —SO$_2$—, —NR$_o$— (wherein R$_o$ represents a hydrogen atom or an alkyl group), —CO—, —CO—NH— or —SO$_2$—NH—.

In principle, the above-described dye moiety may be a moiety of any kinds of dyes. However, the dye moiety should have a sufficient diffusibility so that it passes through the photographic layers in the sensitive material to reach to an image receiving layer. For this purpose, it is possible to bond, if necessary, one or more water solubilizing groups to the dye moiety. Examples of suitable water solubilizing groups include the following groups: a carboxyl group, a sulfo group, a sulfonamide group, a sulfamoyl group, or a hydroxyl group, or an aliphatic or an aromatic group.

Examples of particularly suitable dyes in the present invention include the following dyes: azo dyes, azomethine dyes, anthraquinone dyes, phthalocyanine dyes, indigoid dyes, triphenylmethane dyes, metal complex dyes and colored metal complexes.

The above-noted expression "dye precursor moiety" refers to a moiety of a compound capable of forming a dye in a conventional processing stage of a photographic processing step or in an additional processing stage by release of an auxochromic group (auxochrome) in a color forming system by oxidation (namely, an auxochrome is released and joins in a chromophore). In this case, the dye precursor may be a leuco dye or may be a dye capable of forming another dye.

Examples of Y effective for the redox compounds include N-substituted sulfamoyl groups. For example, as Y, there are groups represented by formula (A).

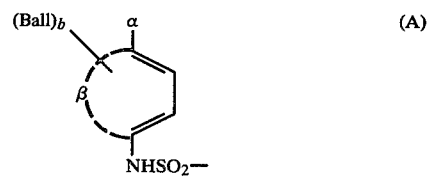

In the formula, β represents a non-metallic atomic group necessary to form a benzene ring which may be condensed with a carbocyclic ring or a heterocyclic ring to form, for example, a naphthalene ring, a quinoline ring, a 5,6,7,8-tetrahydronaphthalene ring or a chroman ring, etc. Further, the above-described benzene ring or the ring formed by condensing a carbocyclic ring or a heterocyclic ring with the benzene ring may be substituted by halogen atoms, alkyl groups, alkoxy groups, aryl groups, aryloxy groups, a nitro group, an amino group, alkylamino groups, amide groups, a cyano group, alkylmercapto groups, a keto group, carboalkoxy groups and heterocyclic groups, etc.

α represents a group represented by —OG$^1$ or —NHG$^2$. Here, G$^1$ represents hydrogen or a group which forms a hydroxyl group by hydrolysis, and, preferably, it is hydrogen or a group represented by

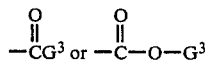

wherein $G^3$ represents an alkyl group, and particularly an alkyl group having from 1 to 18 carbon atoms such as a methyl group, an ethyl group or a propyl group or a halogen substituted alkyl group having from 1 to 18 carbon atoms such as a chloromethyl group or a trifluoromethyl group, etc., a phenyl group or a substituted phenyl group. Further, $G^2$ represents hydrogen, an alkyl group having from 1 to 22 carbon atoms or a hydrolyzable group. A preferred group as the hydrolyzable group of $G^2$ is that represented by

$-SO_2G^5$ or $-SOG^5$ wherein $G^4$ represents an alkyl group having from 1 to 4 carbon atoms such as a methyl group, a halogen substituted alky group such as a trichloromethyl group or a trifluoromethyl group, an alkylcarbonyl group such as an acetyl group, an alkyloxy group, a substituted phenyl group such as a nitrophenyl group or a cyanophenyl group, a phenyloxy group substituted or not substituted by lower alkyl groups or halogen atoms, a carboxyl group, an alkyloxycarbonyl group, an aryloxycarbonyl group, an alkylsulfonylethoxy group or an arylsulfonylethoxy group, and $G^5$ represents a substituted or unsubstituted alkyl group or an aryl group.

Further, b can be 0 or an integer of 1 or 2, provided that b is 1 or 2 and preferably 1, except for the case in which a group corresponding to the above-described alkyl group which renders the compound represented by formula (A) immobile and non-diffusible is introduced as $G^2$ of the $-NHG^2$ moiety for the aforesaid α, i.e., in the case where α is $-OG^1$, and in the case where α is $-NHG^2$ wherein $G^2$ is hydrogen, an alkyl group having 1 to 8 carbon atoms, or a hydrolyzable group. Ball represents a group which makes the compound diffusion resistant.

Examples of this kind of Y have been described in Japanese Patent Applications (OPI) Nos. 33826/73, 50736/78, 54021/79 and 143230/79. Another example of Y suitable for this type of compound is a group represented by formula (B)

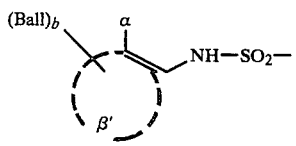

In the formula, Ball, α, and b each has the same meaning as in the case of the formula (A), and β' represents an atomic group necessary to form a carbocyclic ring such as a benzene ring which may be condensed with a carbocyclic ring or a heterocyclic ring to form a naphthalene ring, a quinoline ring, a 5,6,7,8-tetrahydronaphthalene ring or a chroman ring, etc. Further, the above-described various rings may be substituted by halogen atoms, alkyl groups, alkoxy groups, aryl groups, aryloxy groups, a nitro group, an amino group, alkylamino groups, arylamino groups, amido groups, a cyano group, alkylmercapto groups, a keto group, carboalkoxy groups and heterocyclic groups, etc. Examples of this kind of Y have been described in Japanese Patent Application (OPI) No. 113624/76, U.S. Pat. No. 4,053,312 and Japanese Patent Applications (OPI) Nos. 149328/78, 65034/79, 111344/79 and 91187/79.

Couplers useful in the present invention have been described, for example, in *The Theory of Photographic Process* (4th Edition, 1977, edited by T. H. James), Chapter 12. In the following, a case of using the redox compound is illustrated as a representative.

The dye releasing redox compound is coated in an amount of from $1 \times 10^{-4}$ to $1 \times 10^{-2}$ mol/m², and preferably from $2 \times 10^{-4}$ to $2 \times 10^{-3}$ mol/m².

The dye releasing redox compounds used in the present invention can be dispersed in hydrophilic colloids as carriers by various methods according to the type of the compound. For example, compounds having a dissociative group such as a sulfo group or a carboxyl group can be added to the hydrophilic colloid solution after dissolving in water or an aqueous alkaline solution. In the case of dye releasing redox compounds which are difficult to dissolve in aqueous media but are easily soluble in organic solvents, a solution obtained by dissolving them in the organic solvent is added to the hydrophilic colloid solution to disperse into finely divided particles by stirring. As suitable solvents, there are ethyl acetate, tetrahydrofuran, methyl ethyl ketone, cyclohexanone, β-butoxy-β-ethoxyethyl acetate, dimethylformamide, dimethyl sulfoxide, 2-methoxyethanol and tri-n-butylphthalate, etc. In these dispersing solvents, solvents which have a comparatively low vapor pressure may be volatilized when the photographic layers are dried or can be volatilized prior to application by a method described in U.S. Pat. Nos. 2,322,027 and 2,801,171. In these dispersing solvents, solvents which are easily soluble in water can be removed by a water wash process described in U.S. Pat. Nos. 2,949,360 and 3,396,027. In order to stabilize the dispersion of the dye releasing redox compounds and to accelerate the dye image forming step, it is advantageous to incorporate solvents which are substantially insoluble in water and have a boiling point of 200° C. or more at atmospheric pressure into the photographic element together with the dye releasing redox compounds. As the high boiling point solvents suitable for this purpose, there are aliphatic esters such as triglyceride of higher aliphatic acids or dioctyl adipate, phthalic acid esters such as di-n-butylphthalate, phosphoric acid esters such as tri-o-cresyl phosphate or tri-n-hexyl phosphate, amides such as N,N-diethyllaurylamide, and hydroxy compounds such as 2,4-di-n-amylphenol, etc. Furthermore, in order to stabilize the dispersion of the dye releasing redox compounds and to accelerate the dye image forming step, it is advantageous to incorporate hydrophilic polymers in the photographic element together with the dye releasing redox compounds. Examples of hydrophilic polymers suitable for this purpose include shellac, phenol-formaldehyde condensate, poly-n-butyl acrylate, copolymer of n-butyl acrylate and acrylic acid, and copolymer of styrene and methacrylamide, etc. These polymers may be dispersed in the hydrophilic colloid after dissolving in an organic solvent together with the dye releasing redox compounds, or a hydrosol of the polymers prepared by emulsion polymerization may be added to a hydrophilic colloid dispersion of the dye releasing redox compounds. Generally, dispersion of the dye releasing redox compounds are effectively attained under a high shearing force. The dispersion of the dye releasing redox compounds is remarkably promoted by using surface active agents as emulsifiers. As the surface active agents useful for dispersing the dye releasing redox compounds used in the present invention, there are sodium triisopropylnaphthalenesulfonate, sodium dinonylnaphthalenesulfonate, sodium p-dodecylbenzenesulfonate, sodium dioctylsulfosuccinate, sodium cetylsulfate and anionic surface active agents described in Japanese Patent Publication No. 4293/64. When these anionic surface active agents are used together with higher aliphatic acid esters of anhydrohexitol, a particularly excellent dispersibility is exhibited, as disclosed in U.S. Pat. No. 3,676,141.

In a preferred step for producing a composition containing the polymer having a repeating unit represented by formula (I) used in the present invention, the polymer is dissolved in a volatile organic solvent (for example, ethyl acetate) when it is insoluble in water but soluble in organic solvents. The resulting solution is then emulsified in a sol of a hydrophilic binder such as gelatin to obtain an emulsion wherein small drops of the solution of the polymer in the volatile solvent are finely dispersed in the aqueous phase. This composition is solidified by, for example, cooling. From the solidified composition in a noodle state, substantially whole amounts of the solvent are removed by evaporation at room temperature or by washing. Thus, an emulsion wherein polymer particles are uniformly dispersed in the hydrophilic colloid as a binder is obtained. These particles are preferred to have an average particle size in the range of from about 0.2 to 3μ.

This polymer dispersion may contain, if necessary (e.g., in order to control the activity of the polymer as a scavenger) solvents having a high boiling point or another synthetic polymers which are insoluble in water but soluble in organic solvents (for example, polyvinyl acetate or polymethyl methacrylate, etc.).

In the case that the polymer used in the present invention is hydrophilic and is soluble in water or water-miscible solvents having a low boiling point (for example, methanol), the solution of the polymer is added directly to the hydrophilic binder, by which the desired dispersion can be prepared.

In another step, a polymer dispersion obtained by emulsion polymerization for the polymer used in the present invention is mixed directly with the hydrophilic binder, by which the desired dispersion can be prepared.

A preferred embodiment of the invention comprises the use of a polymer within the scope of the invention in the form of latex (i.e., as an emulsion), or the form of a latex mixture (a mixture of a latex of the invention polymer and a latex of a polymer(s) other than the invention polymers), and results in improved film strength. Examples of such other polymers include PVA, polymethyl methacrylate, etc.

Examples of the hydrophilic colloids used for dispersing the oxidized developing agent scavenger used in the present invention and the dye releasing redox compound used in the present invention include gelatin, colloidal albumin, casein, cellulose derivatives such as carboxymethyl cellulose or hydroxyethyl cellulose, etc., saccharide derivatives such as agar, sodium alginate or starch derivatives, etc., and synthetic hydrophilic colloids such as polyvinyl alcohol, poly-N-vinylpyrrolidone, polyacrylic acid copolymer, polyacrylamide or derivatives of them (for example, partially hydrolyzed products), etc. If necessary, a compatible mixture of two or more of these colloids is used. Among them, the most generally used is gelatin, but a part or all of the gelatin may be substituted by synthetic hydrophilic colloids.

Examples of the dye releasing redox compounds having a dye constitution moiety containing a reducible group in the dye structural part have been described in Japanese Patent Applications (OPI) Nos. 126331/74, 109928/76 and 99431/79.

A process for obtaining color diffusion transfer images by means of the dye releasing redox compound has been described in *Photographic Science and Engineering*, Vol. 20, No. 4, pages 155–164, July/August, 1976.

In the above-described process, any silver halide developing agent can be used, if the dye releasing redox compound can be subjected to cross-oxidation by it. Such a developing agent may be contained in an alkaline processing composition, or may be contained in a layer of the photographic element. Examples of the developing agents capable of use in the present invention include the following.

Hydroquinones, aminophenols (for example, N-methylaminophenol), pyrazolidinones (for example, phenidone, 1-phenyl-3-pyrazolidinone, 1-phenyl-4,4-dimethyl-3-pyrazolidinone, 1-p-tolyl-4-methyl-4-oxymethyl-3-pyrazolidinone, 1-(4'-methoxyphenyl)-4-methyl-4-oxymethyl-3-pyrazolidinone and 1-phenyl-4-methyl-4-oxymethyl-3-pyrazolidinone), and phenylenediamines (for example, N,N-diethyl-p-phenylenediamine, 3-methyl-N,N-diethyl-p-phenylenediamine and 3-methoxy-N-ethoxy-p-phenylenediamine), etc.

Among the above-described compounds, white-and-black developing agents which have a property of reducing formation of stains in the image receiving layer (particularly, pyrazolidinones) are particularly preferable to color developing agents such as phenylenediamines, etc.

The processing composition contains bases such as sodium hydroxide, potassium hydroxide, sodium carbonate or sodium phosphate and has an alkalinity of pH 9 or more and preferably pH 11.5 or more. The processing composition can contain antioxidants such as sodium sulfite, ascorbic acid salts or piperidinohexose reduction, and may contain a controller for silver ion concentration such as potassium bromide. Further, it may contain compounds for increasing viscosity such as hydroxyethyl cellulose or sodium carboxymethyl cellulose.

Further, the alkaline processing composition may contain compounds which accelerate development or accelerate diffusion of dyes (for example, benzyl alcohol, etc.).

In the photosensitive element capable of applying the present invention, the silver halide emulsions are combined with the dye image donators. Combinations of spectral sensitivity of the silver halide emulsion and spectral absorption of the dye image are suitably selected according to the intended color reproduction. Reproduction of natural color by a subtractive process is carried out using photosensitive elements comprising at least two combinations of an emulsion having a selective spectral sensitivity in a certain wavelength range and a dye image donator having a selective spectral absorption in the same wavelength range. It is particularly useful to use photosensitive elements comprising a combination of a blue-sensitive silver halide emulsion and a yellow dye releasing redox compound, a combination of a green-sensitive silver halide emulsion and a magenta dye releasing redox compound and a combination of a red-sensitive emulsion and a cyan dye releasing redox compound. In order to prevent undesirable interaction between combination units of emulsion each having a different spectral sensitivity, an intermediate layer is provided therebetween.

These combination units of the emulsion and the dye releasing redox compound may be applied in layers so as to have a face-to-face relation in the photosensitive element or they may be granulated (the dye releasing redox compound and the silver halide particle are existent in the same grain) and applied as a mixture of grains to form a monolayer.

A barrier layer may be provided between the intermediate layer and the layer containing a dye image donator, as described in Japanese Patent Application (OPI) No. 52056/80. Further, the silver halide emulsion may be added to the intermediate layer as described in Japanese Patent Application No. 14155/79.

As mordant layers, neutralization layers, layers for controlling a neutralization rate (timing layer) and processing compositions, etc., capable of using for the photosensitive materials for a color diffusion transfer process of the present invention, it is possible to use those described, for example, in Japanese Patent Application (OPI) No. 64533/77.

The photosensitive materials for a color diffusion transfer process of the present invention are preferred that they are monosheet type film units (combination of a photosensitive element, an image receiving element and a processing element) unified in a body before, during and after the exposure, which can be developed in the light. Such film units have been described in *Photographic Science and Engineering* and *Neblette's Handbook of Photography and Reprography Materials, Process and Systems,* Seventh Ed. (1977), Chapter 12, etc.

The color photographic materials of the present invention can be used, of course, for not only a color diffusion transfer process, but also a conventional color photographic process.

EXAMPLE—COMPARATIVE EXPERIMENT

The following layers were applied in turns to a polyethylene terephthalate base to produce Sample 1-1.

(1) A light reflection layer containing 44 g/m² of titanium dioxide and 4.4 g/m² of gelatin.

(2) A layer containing 0.65 g/m² of Polymer (1) and 0.8 g/m² of gelatin.

Likewise, Samples 1-2, 1-3 and 1-4 and Comparative Samples 1-5 and 1-6 were produced.

Sample 1-2: The same as Sample 1-1, except that Polymer (2) was applied so that the equivalent of hydroquinone moiety was equal to that of Sample 1-1.

Sample 1-3: The same as Sample 1-2, except that Polymer (13) was used.

Sample 1-4: The same as Sample 1-2, except that Polymer (17) was used.

Sample 1-5: The same as Sample 1-1, except that the compound described in Japanese Patent Application (OPI) No. 29637/79, viz., 2,5-di-t-pentadecylhydroquinone, was applied as the hydroquinone in the same equivalent amount as in Sample 1-1.

Sample 1-6: The same as Sample 1-1, except that 2,5-disec-dodecylhydroquinone, described in U.S. Pat. No. 3,700,453, was used.

After these Samples 1-1 to 1-6 were preserved under atmospheric condition for 7 days (Condition A) and at 60° C. and 80% RH for 3 days (Condition B), the state of the surface and degree of coloration were compared.

TABLE 1

| Sample No. | Degree of Coloration Coloration Reflective Density (blue filter) | | Note |
| --- | --- | --- | --- |
| | Condition A | Condition B | |
| 1-1 | 0.19 | 0.20 | This Invention |
| 1-2 | 0.19 | 0.20 | " |
| 1-3 | 0.19 | 0.20 | " |
| 1-4 | 0.19 | 0.21 | " |
| 1-5 | 0.20 | 0.40 | Comparison |
| 1-6 | 0.21 | 0.37 | " |

It is understood from the results shown in Table 1 that the comparative samples became highly colored under Condition B, but samples using the polymers of the present invention scarcely colored. It is believed that the coloration is caused by oxidation of hydroquinone derivatives.

EXAMPLE 1

The following layers were applied in turns to a transparent polyethylene terephthalate film base to produce a photosensitive material (I).

(1) A mordant layer containing 3.0 g/m² of copoly(styrene-N-vinylbenzyl-N,N,N-trihexylammonium chloride) and 3.0 g/m² of gelatin.

(2) A light reflection layer containing 20 g/m² of titanium dioxide and 2.0 g/m² of gelatin (3) A light shielding layer containing 3.0 g/m² of carbon black and 2.0 g/m² of gelatin.

(4) A layer containing a cyan dye releasing redox compound having the following structure (0.44 g/m²), tricyclohexylphosphate (0.09 g/m²) and gelatin (0.8 g/m²).

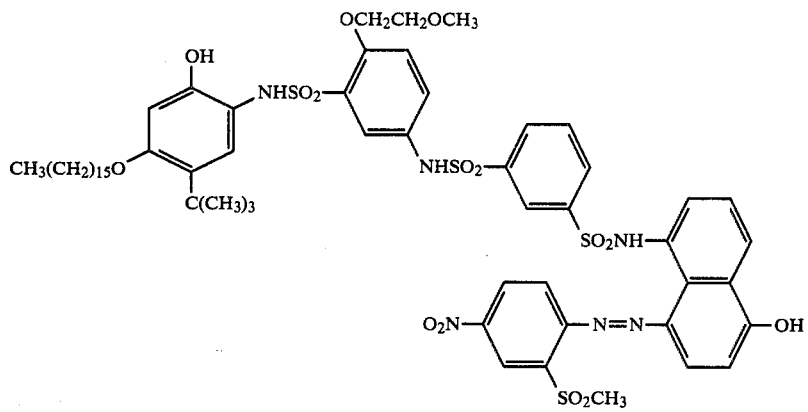

(5) A layer containing a red-sensitive inner latent image type direct reversal silver bromide emulsion (10.3 g/m² as silver), gelatin (1.2 g/m²), a nucleus forming agent having the following structural formula (0.05 mg/m²) and sodium salt of 2-sulfo-5-n-pentadecylhydroquinone (0.13 g/m²).

(6) A layer containing 0.73 g/m² of Polymer (1) used in the present invention and 0.4 g/m² of gelatin.

(7) A layer containing a magenta dye releasing redox compound having the following structural formula I (0.21 g/m²), a magenta dye releasing redox compound having the structural formula II (0.11 g/m²), tricyclohexylphosphate (0.08 g/m²) and gelatin (0.9 g/m²).

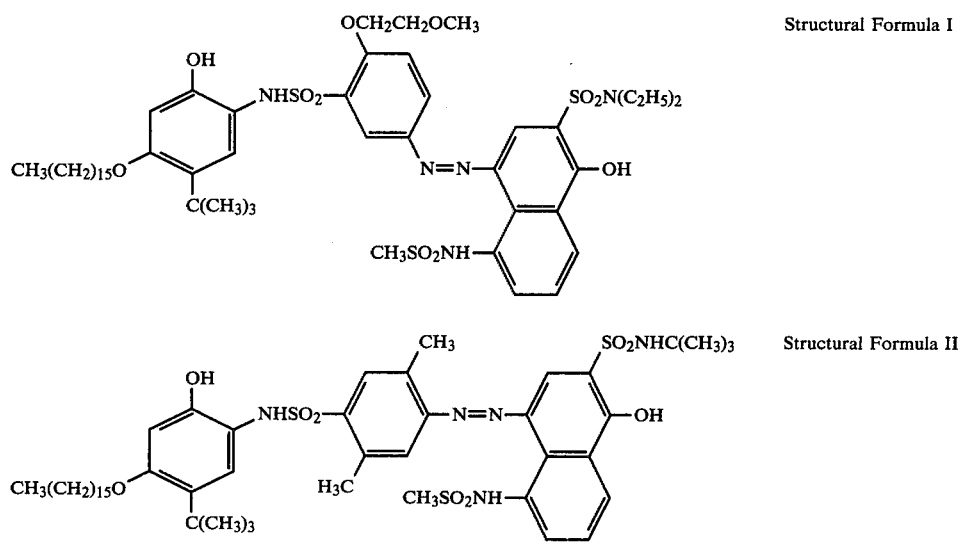

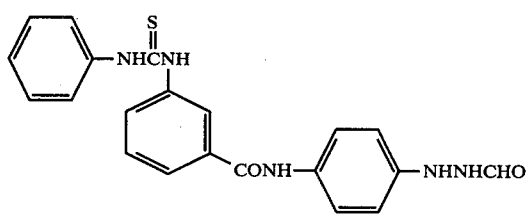

(8) A layer containing a green-sensitive inner latent image type direct reversal silver bromide emulsion (0.82 g/m² as silver), gelatin (0.9 g/m²), the same nucleus forming agent as in the layer (5) (0.03 mg/m²) and sodium salt of 2-sulfo-5-n-pentadecylhydroquinone (0.08 g/m²).

(9) The same layer as the layer (6).

(10) A layer containing a yellow dye releasing redox compound having the following structural formula (0.53 g/m²), tricyclohexyl phosphate (0.13 g/m²) and gelatin (0.7 g/m²).

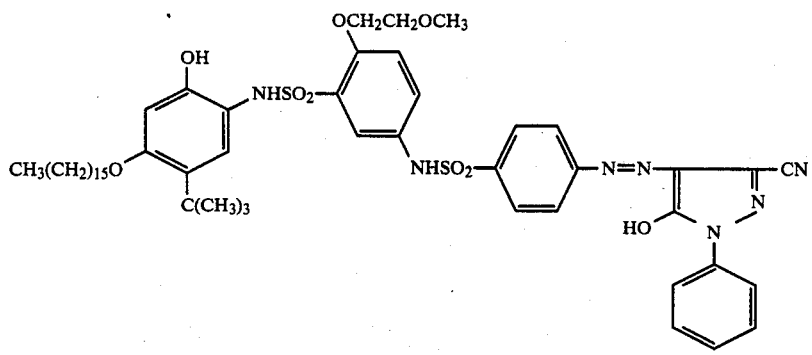

(11) A layer containing a blue-sensitive inner latent image type direct reversal silver bromide emulsion (1.09 g/m²) as silver), gelatin (1.1 g/m²), the same nucleus forming agent as that in the layer (5) (0.04 mg/m²) and sodium salt of 2-sulfo-5-n-pentadecylhydroquinone (0.07 g/m²).

(12) A layer containing gelatin (1.0 g/m²).

The following layers (1') to (3') were applied in turns to a transparent polyester base to produce a cover sheet.

(1') A layer containing an 80:20 (ratio by weight) copolymer of acrylic acid and butyl acrylate (22 g/m²) and 1,4-bis(2,3-epoxypropoxy)butane (0.44 g/m²).

(2') A layer containing acetylcellulose (39.4 g of acetyl group was formed by hydrolyzing 100 g of acetylcellulose) (3.8 g/m²), a 60:40 (ratio by weight) copolymer of styrene and maleic acid anhydride (molecular weight: about 50,000) (0.2 g/m²) and 5-(β-cyanoethylthio)-1-phenyltetrazole (0.115 g/m²).

(3') A layer containing an 85:12:12:3 (ratio by weight) copolymer latex of vinylidene chloride, methyl acrylate and acrylic acid (2.5 g/m²) and a polymethyl methacrylate latex (particle size: 1 to 3 μm) (0.05 g/m²).

The following processing solution was prepared.

| 1-p-Tolyl-4-hydroxymethyl-4-methyl-3-pyrazolidone | 6.9 g |
| Methylhydroquinone | 0.3 g |
| 5-Methylbenzotriazole | 3.5 g |
| Sodium sulfite (anhydrous) | 0.2 g |
| Na+ salt of carboxymethyl cellulose | 58 g |
| Potassium hydroxide (28% aq. soln.) | 200 cc |
| Benzyl alcohol | 1.5 cc |
| Carbon black | 150 g |
| Water | 685 cc |

After the above-described photosensitive sheet was exposed to light (8 CMS) through a multicolor wedge, it was unified with a container containing the above-described processing solution and the cover sheet in a body, and the processing solution was spread by means of a pressing member so as to have a thickness of 80 microns, to thereby obtain a transfer color image. After four minutes, an excellent multicolor image could be observed through the base of the photosensitive sheet. Color separation was excellent and hues of cyan and green were particularly excellent.

EXAMPLE 2

As a comparative sample for the photosensitive material (I) of the present invention described in Example 1, a comparative photosensitive material (II) having the same layer construction as that of photosensitive material (I) was produced, but the layers (6) and (9) in the photosensitive material (I) were replaced with the following layers (6') and (9'), respectively.

Layer (6'): A color stain preventing agent contained layer which contained 2,5-di-t-pentadecylhydroquinone (1.0 g/m²) and gelatin (0.8 g/m²).

Layer (9'): The same layer as layer (6').

Likewise, a comparative photosensitive material (III) was produced with using the following:

Layer (6''): A color stain preventing agent contained layer which contained Compound A (1.2 g/m²) and gelatin (0.8 g/m²).

Layer (9''): The same layer as layer (6'').

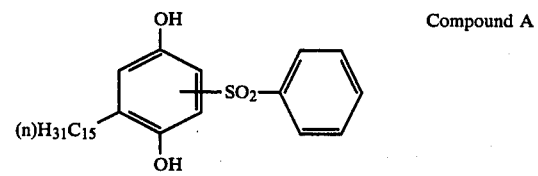

Compound A

After being preserved in a room (25° C., 60% RH) for 3 days or at 45° C. and 70% RH for 3 days, the photosensitive materials (I), (II) and (III) were exposed to light and subjected to spreading of the processing solution in the same manner as in Example 1. After one day, densities of the transfer color image were measured by a color densitometer. The results are shown in Table 2.

TABLE 2

| | Condition of Preservation | | | |
| | In Room (25° C., 60% RH) for 3 Days | | At 45° C., 70% RH for 3 Days | |
| | Reflection Density after One Hour after Processing | | Reflection Density after One Hour after Processing | |
| Photosensitive Material | Maximum Density | Minimum Density | Maximum Density | Minimum Density |
| Photosensitive material (I) | | | | |
| Yellow density | 1.82 | 0.24 | 1.80 | 0.24 |
| Magenta density | 2.05 | 0.21 | 2.04 | 0.21 |
| Cyan density | 1.98 | 0.30 | 1.96 | 0.30 |
| Comparative | | | | |

TABLE 2-continued

| | Condition of Preservation | | | |
|---|---|---|---|---|
| | In Room (25° C., 60% RH) for 3 Days | | At 45° C., 70% RH for 3 Days | |
| | Reflection Density after One Hour after Processing | | Reflection Density after One Hour after Processing | |
| Photosensitive Material | Maximum Density | Minimum Density | Maximum Density | Minimum Density |
| photosensitive material (II) | | | | |
| Yellow density | 1.80 | 0.24 | 1.67 | 0.24 |
| Magenta density | 1.88 | 0.24 | 1.15 | 0.22 |
| Cyan density | 1.68 | 0.30 | 1.23 | 0.29 |
| Comparative photosensitive material (III) | | | | |
| Yellow density | 1.74 | 0.24 | 1.62 | 0.24 |
| Magenta density | 1.90 | 0.21 | 1.35 | 0.22 |
| Cyan density | 1.72 | 0.30 | 1.54 | 0.33 |

As is clear from the results shown in Table 2, in the photosensitive material (I) of the present invention, the maximum densities of the resulting yellow, magenta, and cyan transfer dyes were high and stable under both conditions of preservation. On the contrary, in the comparative photosensitive material (II), the maximum densities were lower than those of the photosensitive material (I) under both conditions of preservation and, particularly, the maximum densities of the transfer image were significantly reduced. Also in material (II), color stains occurred and color separation deteriorated under the more severe condition of preservation.

Further, when the reactions of the photosensitive materials (I) and (II) preserved at 45° C. and 70% RH for 3 days were observed under a microscope, the boundary between the color stain preventing agent contained layer and the dye image donative compound containing layer was distinct in the photosensitive material (I). On the contrary, in the photosensitive material (II), the boundary between them was indistinct, by which it was understood that the color stain preventing agent used migrated into the dye image donative compound containing layer, and the color image donative compound migrated into the color stain preventing agent containing layer.

EXAMPLE 3

The following layers were applied sequentially to a transparent polyester base to produce a photosensitive material 3-1.

(1)–(5): The same layers as those in Example 1.

(6): A layer containing Polymer (1) 0.65 g/m and 0.8 g/m² of gelatin.

Likewise, photosensitive materials 3-2, 3-3 and 3-4 and comparative photosensitive materials 3-5 and 3-6 were produced.

Photosensitive material 3-2: The same sample as Sample 3-1, except that Polymer (2) was applied so that the equivalent of hydroquinone moiety was equal to that of Sample 3-1.

Photosensitive material 3-3: The same sample as described above, except that Polymer (3) was used.

Photosensitive material 3-4: The same sample as described above, except that Polymer (11) was used.

Photosensitive material 3-5: The same sample as the photosensitive material 3-1, except that the compound described in Japanese Patent Application (OPI) No. 29637/79: 2,5-di-t-pentadecylhydroquinone was applied as a hydroquinone derivative in an equimolar amount.

Photosensitive material 3-6: The same sample as described above, except that 2,5-di-sec-dodecylhydroquinone described in U.S. Pat. No. 3,700,453 was used.

After the above-described photosensitive materials were exposed to light through an optical wedge, they were subjected to spread processing at 25° C. using the same cover sheet and the same processing solution as described in Example 1. After 1 day, the cyan transfer image density was measured by a color densitometer and results shown in Table 3 were obtained. (Red filter density is shown as Dr and Green filter density is shown as Dg.)

TABLE 3

| Sample | Value of Dg in case of Dr = 1.0 | Note |
|---|---|---|
| Photosensitive material 3-1 | 0.33 | This Invention |
| Photosensitive material 3-2 | 0.33 | " |
| Photosensitive material 3-3 | 0.33 | " |
| Photosensitive material 3-4 | 0.34 | " |
| Photosensitive material 3-5 | 0.42 | Comparison |
| Photosensitive material 3-6 | 0.51 | " |
| Sample dyed by a cyan color | 0.33 | * |

*A sample dyed by dipping a coated material having the layers (1) to (3) of this example in a solution prepared by dissolving the following cyan dye in a 0.1N NaOH solution was used as the sample dyed with a cyan dye.

It is preferable for the cyan hue that the value of Dg/Dr is lower. Thus it is understood from Table 3 that the photosensitive materials 3-1 to 3-4 using compounds of the present invention have a Dg value in case of Dr=1.0 which is near that of the sample dyed with a cyan color, as compared with comparative samples 3-5 and 3-6, which means that the color stain of the cyan color image occurs to a lesser extent.

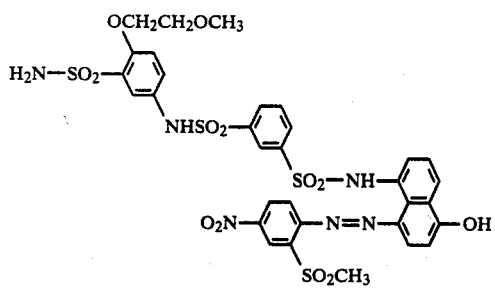

EXAMPLE 4

Test for interlayer adhesive strength between intermediate layer and coloring layer Photosensitive material (I) and photosensitive material (II) described in Example 2 were compared by measuring stripping strength as a criterion of the interlayer adhesive strength. As samples, those preserved under an atmospheric condition (A) (25° C., 60% RH) for 7 days and those preserved under a promoting condition (B) (60° C., 80% RH) for 3 days were used.

In order to measure the stripping strength, the following conditions were adopted.

Measuring apparatus: Instron tensile testing machine (Friction pull tester)

Pulling speed: 300 mm/min.
Stripping angle: 180°
Stripping width: 20 mm
Environmental condition: 25° C., 60% RH (measurement was carried out after the sample was allowed to stand under this condition for 2 hours or more)

TABLE 4

| Results of Measuring Stripping Strength*[3] | | |
|---|---|---|
| Photosensitive Material | (A) | (B) |
| Photosensitive Material (I) | 2.5 kg/20 mm*[1] | 2.5 kg/20 mm*[2] |
| Photosensitive Material (II) | 0.8 kg/20 mm | 0.2 kg/20 mm |

*[1]Separation did not occur in the photosensitive material, but did occur between the photosensitive material and the adhesive tape.
*[2]Separation did not occur in the photosensitive material, but did occur between the photosensitive material and the adhesive tape.
*[3]Average values of four tests.

As is shown in Table 4, under the testing condition, the photosensitive material (I) did not cause separation in the photosensitive material and had strong interlayer adhesion, while the photosensitive material (II) caused separation between layers easily. When a section of the photosensitive material (II) was observed by a microscope after the test was carried out, it appeared that the separation occurred between the color stain preventing layer and the dye releasing redox compound containing layer.

While the invention has been described in detail and with reference to specific embodiments thereof, it will be apparent to one skilled in the art that various changes and modifications can be made therein without departing from the spirit and scope thereof.

What is claimed is:

1. A color photographic sensitive material containing a polymer comprising at least 1 mol% of a repeating unit represented by formula (I)

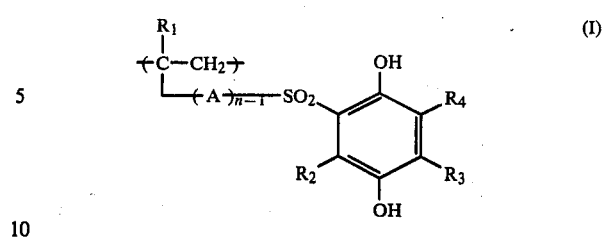

wherein A represents a divalent group, n is 1 or 2, $R_1$ represents hydrogen, a halogen atom or an alkyl group, and $R_2$, $R_3$ and $R_4$ each represents hydrogen, a halogen atom, an alkyl group, an aryl group, an alkoxy group, an aryloxy group, an alkylthio group, an arylthio group, an amino group, an acylamino group, or a sulfonamide group, and $R_3$ and $R_4$ together can form an aromatic ring, provided that the total of carbon atoms of $R_2$, $R_3$, and $R_4$ is 60 or less.

2. A color photographic sensitive material according to claim 1, wherein A in formula (I) is a phenylene group.

3. A color photographic sensitive material according to claim 2, wherein $R_1$ in formula (I) is hydrogen.

4. A color photographic sensitive material according to claim 3, wherein n in formula (I) is 2.

5. A color photographic sensitive material according to claim 3, wherein $R_2$ in formula (I) is hydrogen, and one of $R_3$ and $R_4$ is a substituent other than hydrogen and the other is hydrogen.

6. A color photographic sensitive material according to claim 5, wherein n in formula (I) is 2 and A is a p-phenylene group.

7. A color photographic sensitive material according to claim 6, wherein one of $R_3$ and $R_4$ in formula (I) is a substituted or unsubstituted alkyl group having 20 carbon atoms or less and the other is hydrogen.

8. A color photographic sensitive material according to claim 7, wherein the polymer comprising a repeating unit represented by formula (I) also comprises a repeating unit represented by formula (IA)

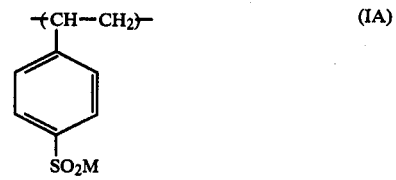

wherein M represents hydrogen or a cation.

9. A color photographic sensitive material according to claim 7, wherein the polymer is used as an emulsion.

10. A color photographic sensitive material according to claim 7, wherein the polymer is used as a polymer dispersion.

11. A color photographic sensitive material according to claim 2, 3, 4, 5, 6, 7, 8, 9, or 10, wherein the color photographic sensitive material is a silver halide photographic sensitive material.

12. A color photographic sensitive material according to claim 1 comprising a photosensitive sheet including an internal latent image type silver halide emulsion layer combined with a dye image forming compound and a layer containing the polymer comprising a repeating unit represented by formula (I) on a base.

13. A color photographic sensitive material according to claim 12, wherein the dye image forming compound is a dye releasing redox compound.

14. A color photographic sensitive material according to claim 13, wherein a dye released from the dye releasing redox compound contains a moiety which is easily reduced.

15. A color photographic sensitive material according to claim 13, which is processable with an alkaline processing composition containing pyrazolidinones as a developing agent.

16. In a monosheet type film unit unified in a body before, during and after exposure which is developable in the light, the improvement comprising a photosensitive sheet used for a color diffusion transfer process including an internal latent image type silver halide emulsion layer combined with a dye releasing redox compound and a layer containing a polymer having a repeating unit represented by formula (I)

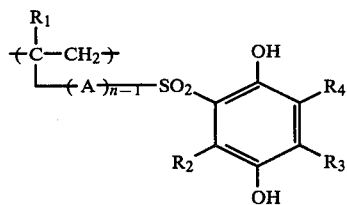

wherein A represents a divalent group, n is 1 or 2, $R_1$ represents hydrogen, a halogen atom or an alkyl group, and $R_2$, $R_3$ and $R_4$ each represents hydrogen, a halogen atom, an alkyl group, an aryl group, an alkoxy group, an aryloxy group, an alkylthio group, an arylthio group, an amino group, an acylamino group, or a sulfonamide group, and $R_3$ and $R_4$ together can form an aromatic ring, provided that the total of carbon atoms of $R_2$, $R_3$, and $R_4$ is 60 or less on a base.

17. A color photographic sensitive material according to claim 12, 13, 14, or 15 which is a color diffusion transfer material.

18. A color photographic sensitive material according to claim 8, wherein the repeating unit represented by formula (IA) constitutes from about 1 to 50 mol% of the polymer.

19. A color photographic sensitive material according to claim 1, 2, 3, 4, 5, 6, 7, 8, 9, or 10, wherein the polymer comprises at least 5 mol% of the repeating unit represented by formula (I).

20. A color photographic sensitive material according to claim 1, 2, 3, 4, 5, 6, 7, 8, 9, or 10, wherein the polymer comprises at least 20 mol% of the repeating unit represented by formula (I).

21. A color photographic sensitive material according to claim 11, wherein the polymer comprises at least 5 mol% of the repeating unit represented by formula (I).

22. A color photographic sensitive material according to claim 11, wherein the polymer comprises at least 20 mol% of the repeating unit represented by formula (I).

* * * * *